(12) United States Patent
Tabacchi

(10) Patent No.: US 6,196,676 B1
(45) Date of Patent: Mar. 6, 2001

(54) SPORTS SPECTACLES

(75) Inventor: Vittorio Tabacchi, Pieve di Cadore (IT)

(73) Assignee: Carrear Optyl Marketing GmbH, Traun (AT)

( * ) Notice: Subject to any disclaimer, the term of this patent is extended or adjusted under 35 U.S.C. 154(b) by 0 days.

(21) Appl. No.: 09/355,414

(22) PCT Filed: Sep. 18, 1998

(86) PCT No.: PCT/EP98/05950

§ 371 Date: Jul. 28, 1999

§ 102(e) Date: Jul. 28, 1999

(87) PCT Pub. No.: WO99/27874

PCT Pub. Date: Jun. 10, 1999

(30) Foreign Application Priority Data

Nov. 28, 1997 (IT) .............................................. PD97A0273

(51) Int. Cl.[7] .................................................. G02C 7/16
(52) U.S. Cl. .............................................................. 351/41
(58) Field of Search ............................... 351/41, 51, 57, 351/140, 153, 154, 123; 2/13, 423, 449, 450, 451

(56) References Cited

U.S. PATENT DOCUMENTS

| 1,686,113 | 10/1928 | Tillyer . | | |
|---|---|---|---|---|
| 1,947,137 | 2/1934 | Fraser . | | |
| 2,519,561 | 8/1950 | Gillman et al. . | | |
| 2,877,463 | 3/1959 | Watkins . | | |
| 5,689,835 | 11/1997 | Chao . | | |
| 5,718,002 | * | 2/1998 | Pavlak | 2/423 |
| 5,760,868 | * | 6/1998 | Jannard et al. | 351/153 |

FOREIGN PATENT DOCUMENTS

| 15 41 307 | 4/1970 | (DE) . |
|---|---|---|
| WO 96 41230 | 12/1996 | (WO) . |
| WO 97 26849 | 7/1997 | (WO) . |

* cited by examiner

*Primary Examiner*—George Manuel
(74) *Attorney, Agent, or Firm*—Sughrue, Mion, Zinn, Macpeak & Seas, PLLC

(57) ABSTRACT

The sports spectacles comprise a lens-carrying frame (10) with an upper cross-member (11) including two branches (11a, 11b) extending symmetrically from a central portion (12) towards respective opposite free ends (13a, 13b) and, on the outer side (8) of each branch, there is a surface (18) with a helical profile extending from a rim (19) for the attachment of the corresponding lens (L), with the helix facing so as to deflect an air-flow striking the corresponding lens (L) towards the respective free end (13a, 13b).

23 Claims, 6 Drawing Sheets

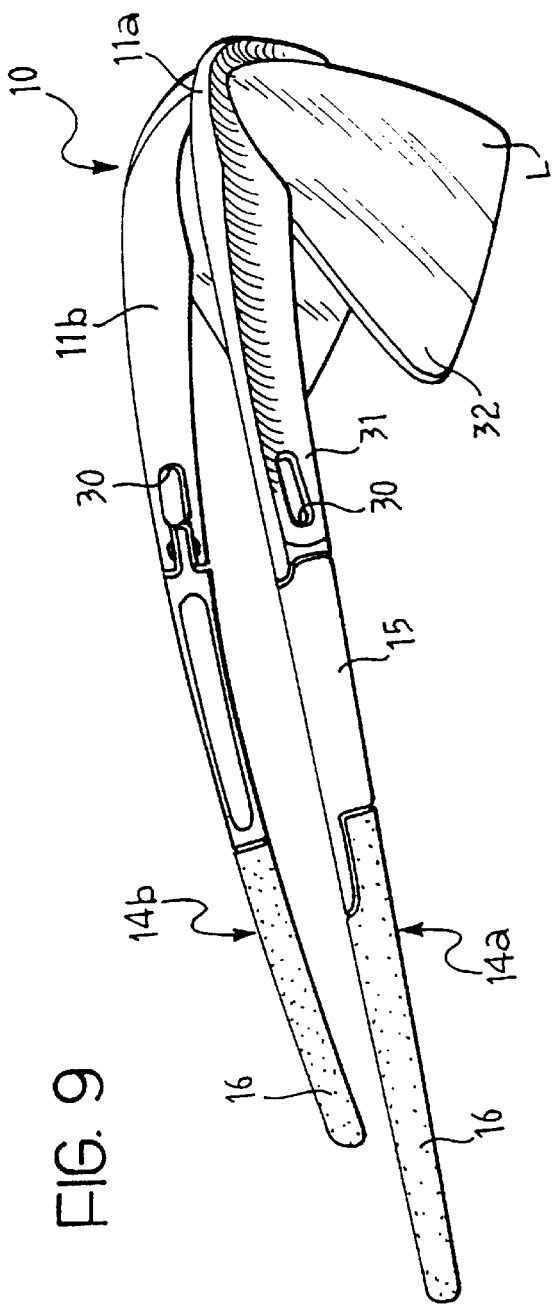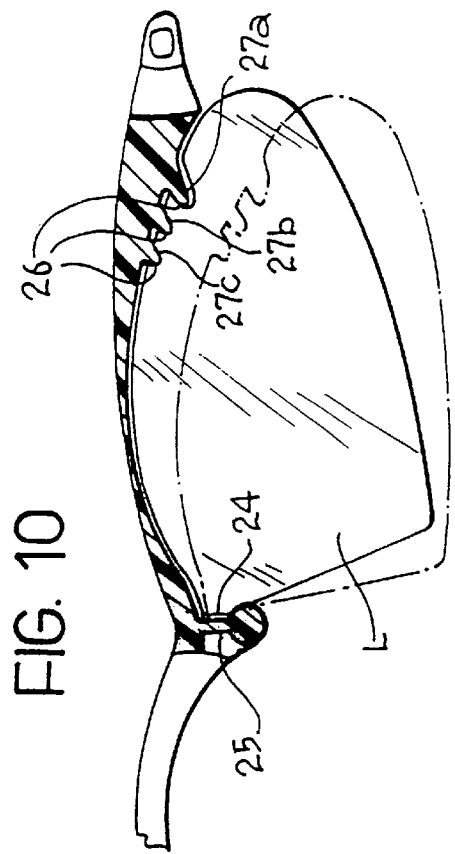

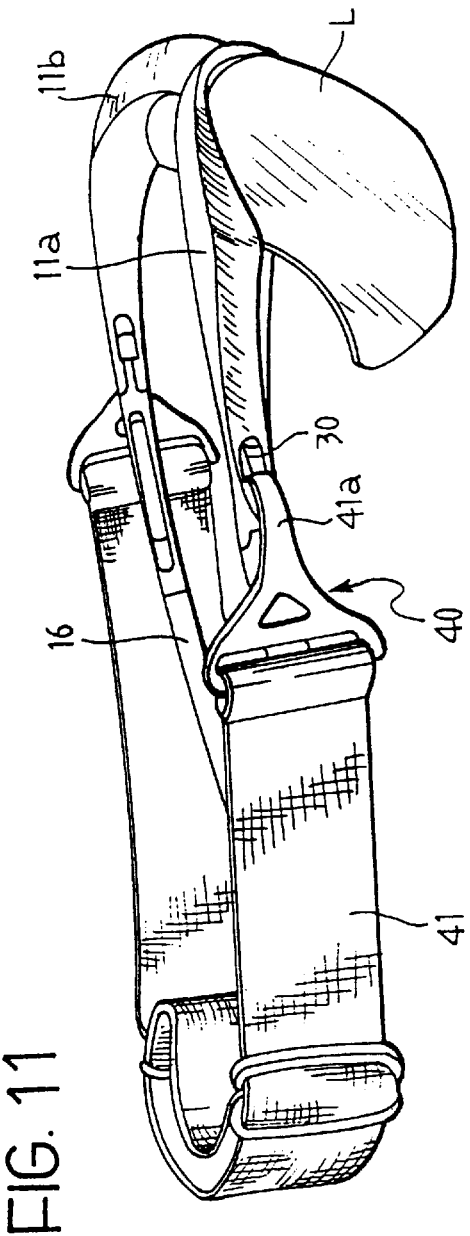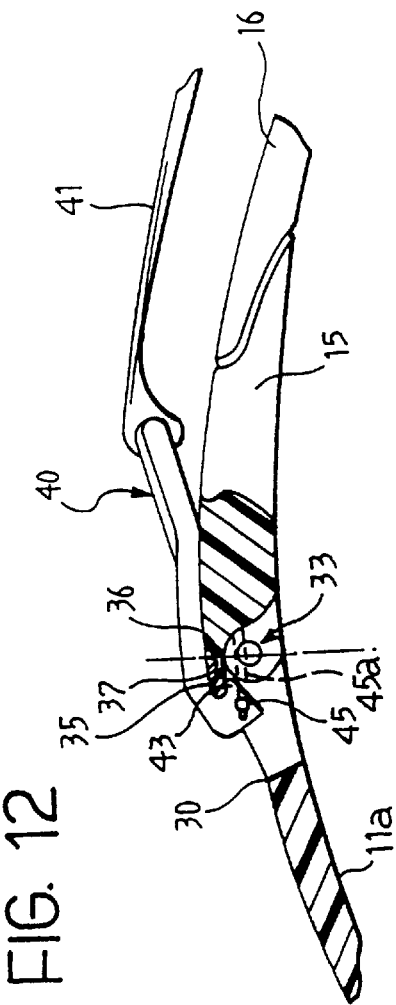
FIG. 11
FIG. 12

SPORTS SPECTACLES

TECHNICAL FIELD

The subject of the present invention is sports spectacles of the type described in the preamble to the main claim.

BACKGROUND ART

Spectacles of this type are widely used for protecting the user's eyes from light, wind, dust and meteorological phenomena, particularly during sports activities.

Many investigations have recently been undertaken in the technical field of sports spectacles with the purpose, amongst other things, of evaluating the effect of the air-flow due to wind (both atmospheric wind and wind due to speed) on the lenses, the ventilation of the internal surfaces of the lenses in order to prevent them from misting up, interaction with the user's field of view, and yet further aspects. For example, it has been found that, regardless of whether the air which strikes the lens is due to meteorological wind or to wind resulting from "speed", it tends to pass over the spectacle frame, creating turbulence on the rear face of the lens, which is troublesome to the user.

DISCLOSURE OF THE INVENTION

The primary object of the present invention is structural and functional improvements to sports spectacles in relation to the aspects listed above. A further object of the invention is to provide sports spectacles which can be adapted easily, by means of various accessories, to a corresponding number of different requirements which may be encountered in various sports disciplines.

These and other objects which will become clear from the following description are achieved by the invention by means of spectacles formed in accordance with the attached claims.

BRIEF DESCRIPTION OF THE DRAWINGS

The characteristics and advantages of the invention will become clearer from the following detailed description of some embodiments thereof, described by way of non-limiting example, with reference to the appended drawings, in which:

FIGS. 8 and 9 are a plan view and a side elevational view of the spectacles of the previous drawings, respectively, FIG. 10 is a section through a detail of the spectacles of the previous drawings taken on the line X—X of FIG. 8 and showing the regions in which each lens is attached to the frame, FIG. 11 is a perspective view of the spectacles of the invention, equipped with a retaining strap, FIG. 12 is a partial section through a detail of the spectacles of FIG. 11, FIGS. 13 to 15 are a front view, a side view and a rear view, respectively, of a detail of the retaining strap of the previous drawings.

BEST MODE OF CARRYING OUT THE INVENTION

Figure 1:
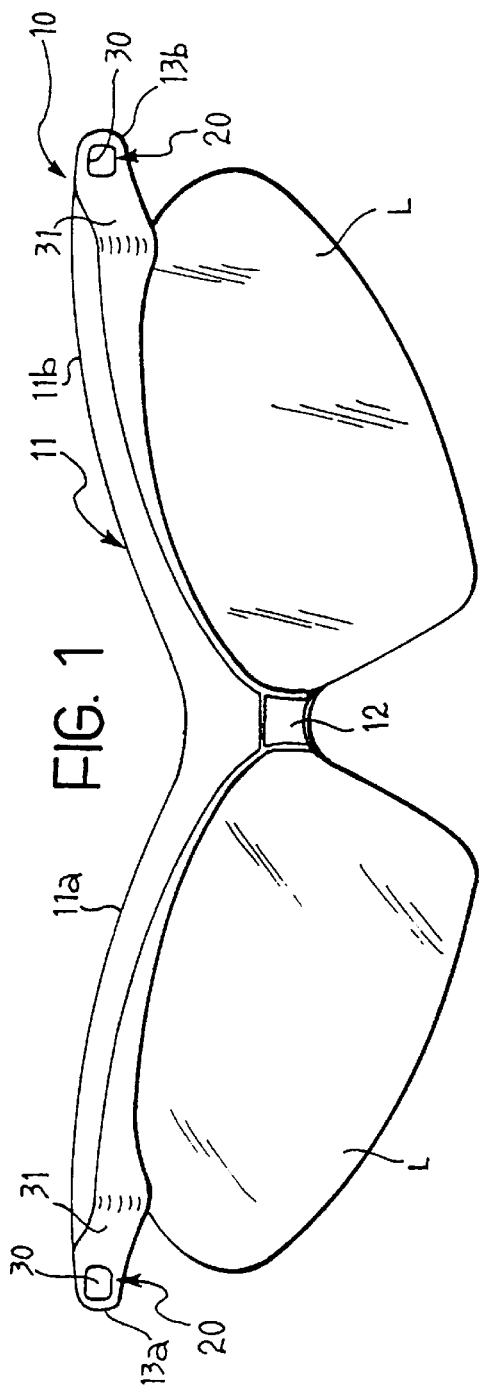
FIG. 1 is a front elevational view of a pair of spectacles formed in accordance with the present invention.

Each of the pairs of spectacles shown in the drawings indicated is equipped with a frame 10 which carries two lenses (both indicated L) and is constituted by an upper cross-member 11 including two branches 11a, 11b extending symmetrically from a central portion 12 towards respective opposite free ends 13a, 13b. A nasal bearing region of the spectacles is defined in the central portion 12 of the cross-member 11.

Respective arms 14a, 14b are articulated to the free ends of the cross-member 11 and each has a metal shaft 15 onto which a soft rubber end element 16 is fitted.

Figure 2:
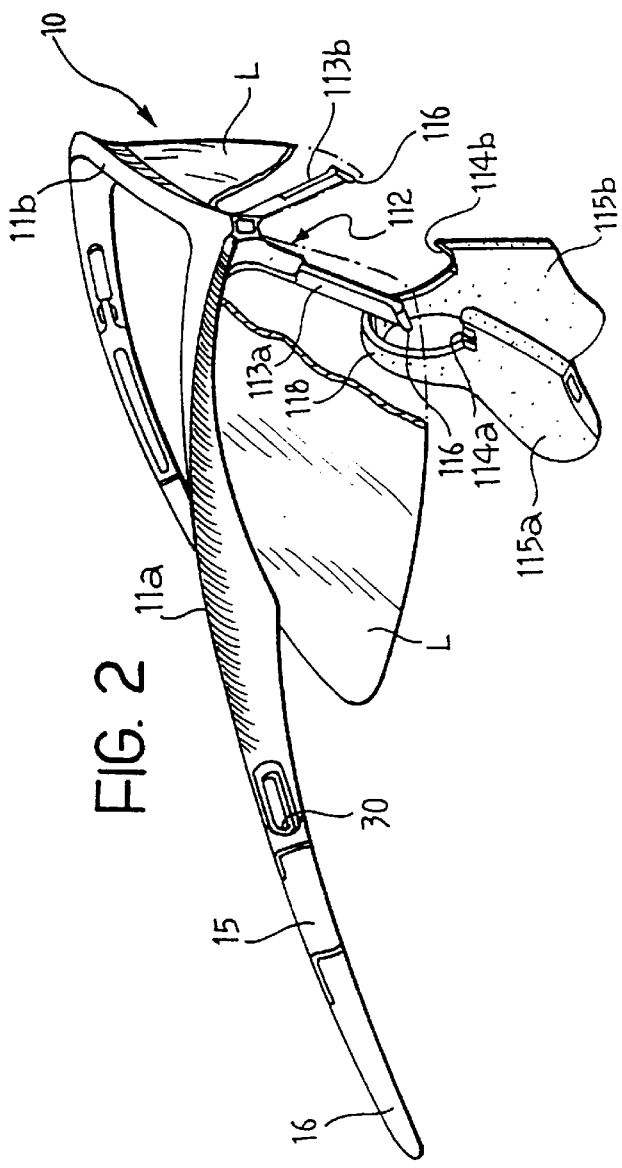
FIG. 2 is a perspective view of the spectacles of the previous drawing with parts partially sectioned and separated.
Figure 8:
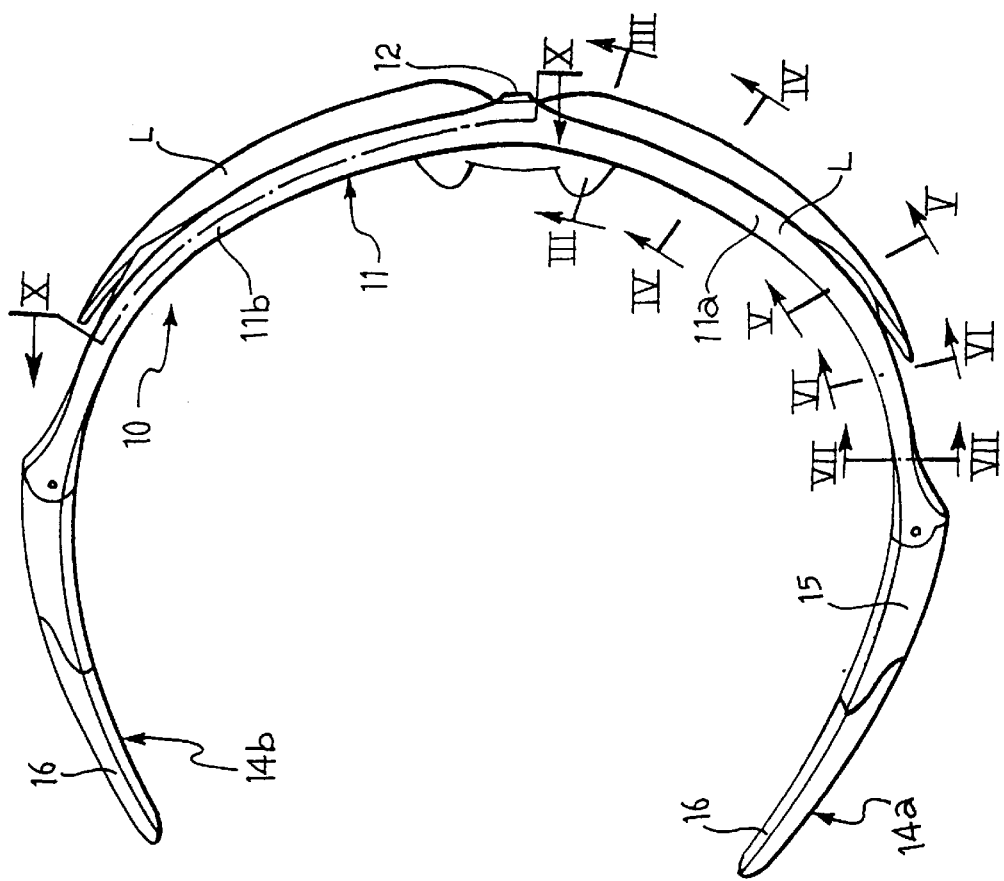
Figure 3:
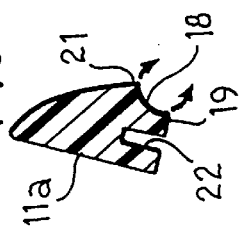
FIGS. 3 to 7 are cross-sections, solely of the upper cross-member of the spectacles of FIG. 1, taken on the lines III—III to VII—VII of FIG. 8, respectively.
Figure 4:
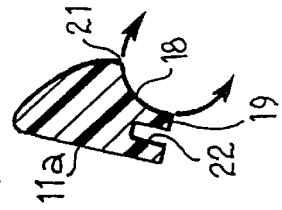
Figure 5:
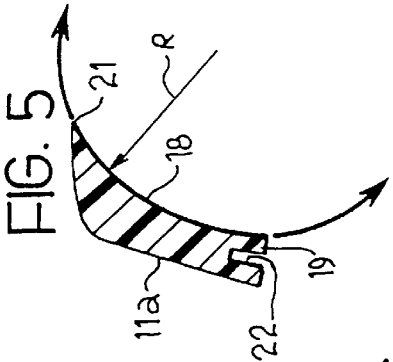
Figure 7:
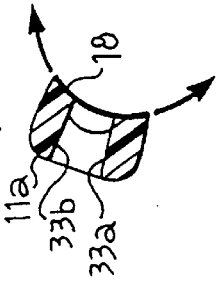
Figure 6:
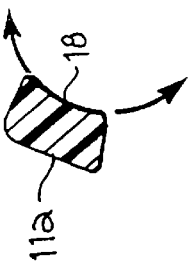

An inner side A which faces the user in use, and an opposite, outer side B are defined in the frame 10. With particular reference to FIGS. 1 to 7, each branch 11a, 11b of the cross-member 11 has, on the outer side B, a surface 18 with a helical profile extending from a rim 19 for the attachment of the corresponding lens L, with the helix facing so as to deflect an air-flow striking the underlying lens L in a manner such as to collect and deflect at least part of the air-flow passing over the upper cross-member 11 and direct it along the corresponding branch 11a, 11b towards flow-discharge means, generally indicated 20, disposed in a discharge position set back on the cross-member towards the corresponding arm 14a, 14b.

The development of the profile of the surface 18 is shown in the cross-sections of FIGS. 3 to 7. As can be seen, it is characterized by a rim 21 which is disposed opposite the rim for the attachment of the corresponding lens and which changes from an orientation substantially perpendicular to the outer surface of the corresponding lens L in the vicinity of the central portion 12 to an orientation almost tangential to the lens L in the vicinity of the discharge means 20. The radius of curvature R of the profile of the surface 18 increases gradually as the surface extends away from the central portion 12.

The rim 19 has a longitudinal groove 22 which houses the facing upper edge of the corresponding lens L; the lens L is restrained releasably on the cross-member 11 so that each lens can easily be replaced by another of a different shape and/or colour in order to adapt the spectacles to different sports disciplines, as will become clearer from the following description. This restraint is achieved by the engagement of a nib 24 projecting from the lens L in a recess 25 defined by an extension of the groove 22 in the central portion of the frame, on one side, and by the engagement of notches 26 in the lens L with respective nibs 27a, 27b, 27c projecting from the groove 22, on the opposite side. At least one of the nibs, specifically that indicated 27a, has a saw-tooth profile which is inclined towards the central portion 12 of the cross-member 11 so that the nib 24 of the lens L is urged resiliently into engagement in the recess 25 and towards a position close to the central portion 12, by means of the resilience of the cross-member 11 and of the lens L.

The discharge means 20 in each discharge position comprises a through-hole 30 between the outer side B and the inner side A of the cross-member 11. The hole 30 opens, on the outer side B, in the region of an approximately spoon-shaped curved surface 31 facing so as to deflect the air-flow received from the helical surface 18 outwardly away from the cross-member 11 and from the corresponding arm 14a, 14b. For this reason, the surface 31 will also be referred to below by the term "deflector 31". This deflector 31 is positioned on the cross-member 11 in a manner such as to extend from the end of the rim 19 for the attachment of the lens as far as the free end of the cross-member 11, approximately at the height of the user's temples.

In the region of the deflector 31, the upper edge of the lens L starts to extend away from the cross-member 11, diverging therefrom to define a lateral appendage 32 of the lens which closes the region of the user's eye socket laterally.

Finally, it can be seen that, on the inner side A of the frame 10, the hole 30 opens in an opening 33 which constitutes the articulation seat of the corresponding arm 14a, 14b. The opening 33 is defined between two cheeks 33a, 33b between which an articulation eye 34 of the arm 14a, 14b is housed. A shoulder 35 extends between the cheeks 33a, 33b and, as well as defining the mouth of the hole on the outer side of the frame 10, bears an abutment surface 36. The surface 36 serves, with a further abutment 37 formed on the shaft 15, to limit the opening-out of the arms.

Figure 13:
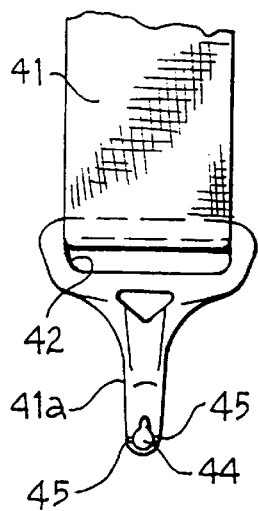
Figure 14:
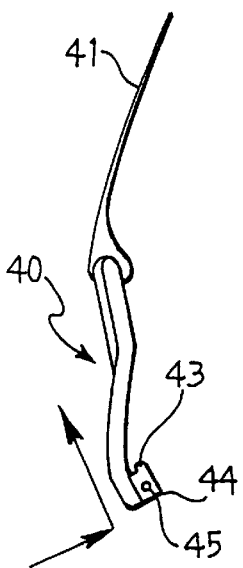
Figure 15:
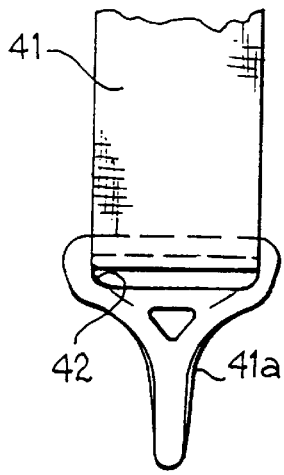
Figure 16:
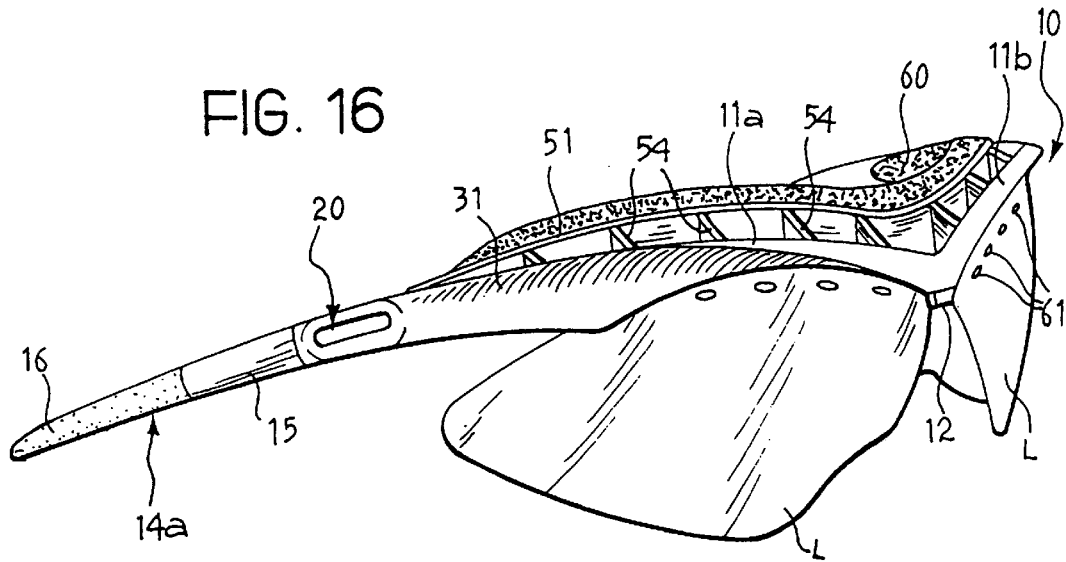
FIG. 16 shows the spectacles of the invention in perspective and equipped with a ventilated spacer element.
Figure 17:
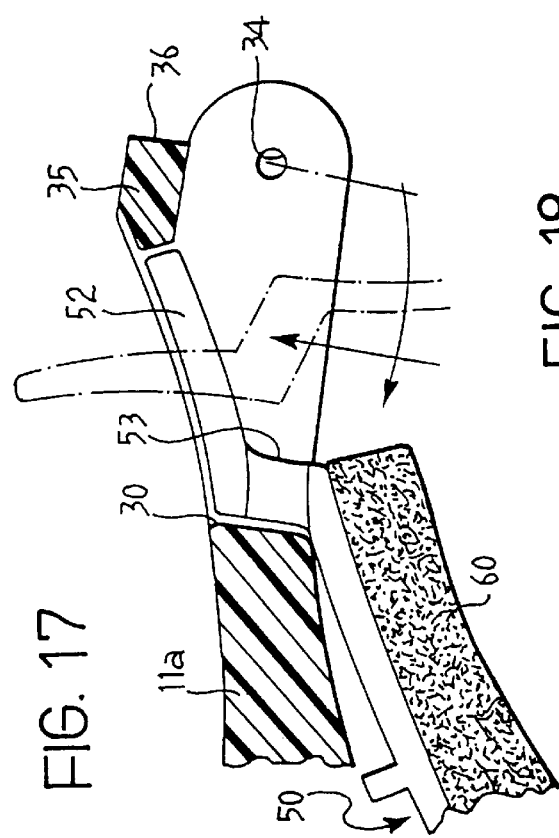
FIG. 17 is a section through a detail of the spectacles of FIG. 16, on an enlarged scale.

With reference to FIGS. 12 to 17, the holes 30 may also serve as engagement means for respective hook elements 40 associated with the opposite ends of a resilient strap 41 which is intended to extend around the back of the user's head in order to hold the spectacles in the operative position during sports activities involving a large amount of movement.

Each hook element 40 comprises a stem 41a, of which one end is fixed, preferably integrally, to a slotted element 42 and the opposite end is slightly bent and carries a tooth-like element 43 extending radially from a cylindrical body 44 which can be housed in the hole 30 bearing against the shoulder 35.

Two small diametrally-opposed, radial appendages 45 project from the body 44 and can snap-engage in corresponding grooves 45a, formed in the cheeks 33a, 33b in order to restrain the hook element 40 in engagement in the corresponding hole 30 whilst permitting limited pivoting relative to the frame 10.

Figure 20:
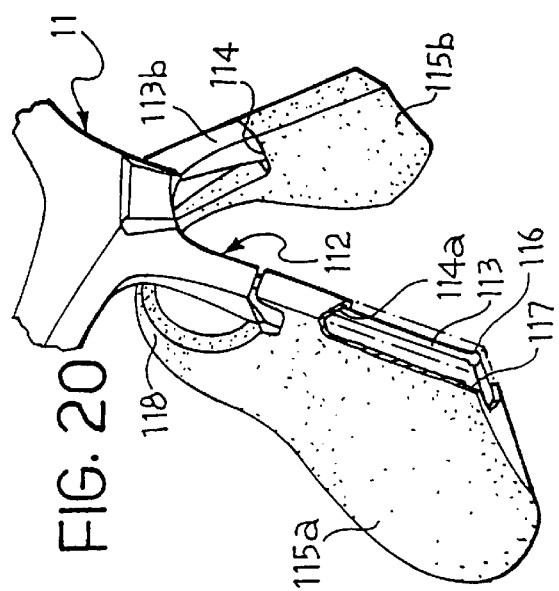
FIG. 20 is a perspective view showing a detail of the spectacles of the previous drawings, on an enlarged scale.
Figure 18:
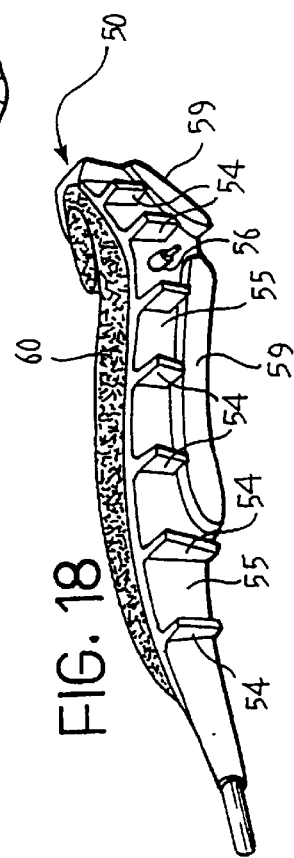
FIGS. 18 and 19 are a perspective view and a plan view, respectively, of the spacer element of the previous drawings.
Figure 19:
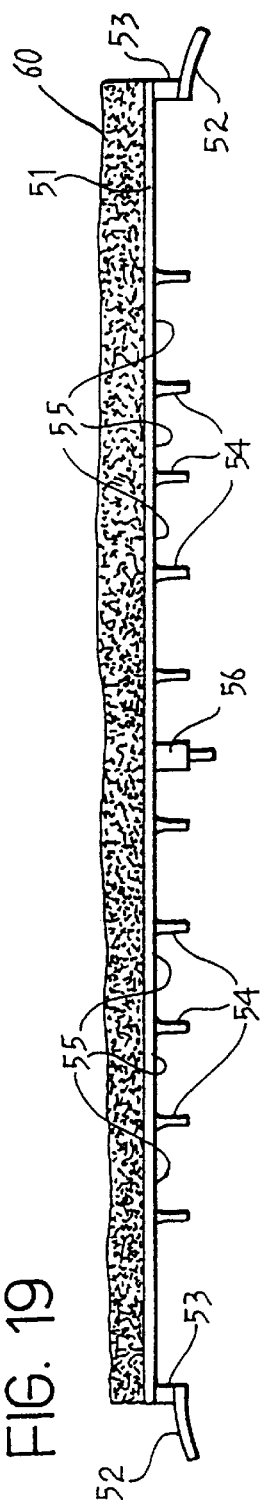

With reference to FIGS. 18 to 23, a further accessory which can be fitted on the spectacles of the invention for use in strong winds and cold climates, for example, during skiing, is a spacer 50 to be fitted releasably on the inner side A of the cross-member 11. The spacer 50 comprises a substantially flexible, strip-like body 51, at the opposite ends of which two respective end elements are formed, each including a key 52 connected to the strip-like body by means of a shoulder 53.

On the side facing the inner side of the cross-member 11, the spacer 50 has a plurality of projections 54 arranged like a comb and spaced by channels 55, as well as a central pin 56 which can be fitted in a hole 57 formed in a facing position in the central portion of the cross-member 11.

In the region of the channels 55 disposed immediately above each lens, or at least for a predominant portion thereof, there is a surface 58 to which a filtering material 59 is applied in order to attenuate the air-flow circulating in the channels 55 in question.

On the opposite side to the cross-member 11, the spacer 50 carries a band 60 of foam rubber or another foamed material which is highly deformable and can adapt to fit the user's face.

The spacer 50 is held on the cross-member 11 by the coupling between the pin 56 and the hole 57 in the centre and by the coupling of the keys 52 and the corresponding shoulders 53 in the holes 30 at the opposite ends.

Finally, it will be noted that, in the embodiment in question, the lenses L have a series of through-holes 61 disposed in the vicinity of the upper edge, approximately in the region of the filtering material 59. The air-flow passing through the holes 61 is thus damped by the filtering material 59.

In the nasal bearing region of the spectacles, there is a nose-piece 112. This nose-piece comprises a pair of cheeks 115a, 115b anchored to the frame 10 by means of two rod-shaped appendages 113a, 113b which straddle the supporting region of the user's nose and each of which can be inserted in a corresponding seat 114a, 114b formed in the respective cheek 115a, 115b. The cheeks 115a, 115b are thus fitted at least partially onto the respective appendages 113a, 113b.

Coupling means are provided on the appendages 113a, 113b and in the seats 114a, 114b for restraining each cheek in its position fitted on the respective appendage. The coupling means are constituted by an enlargement 116 at the free end of each appendage 113a, 113b and by a recess 117 in the vicinity of the free edge of the corresponding seat. The seats 114a, 114b have an open tubular shape for this purpose.

Preferably, the cheeks are made of resilient material such as silicone rubber or equivalent materials and the appendages are made of rigid or semi-rigid plastics material moulded integrally with the upper cross-member of the frame and constitute a reinforcement for the nose-piece, for stiffening the corresponding cheeks.

In a further preferred configuration, the cheeks 115a, 115b are joined by a flexible bridge 118 and are interchangeable with other cheeks of different sizes in order to adapt the spectacles to different morphological configurations of the user's face or to different uses of the spectacles.

The invention thus achieves the proposed object and affords many advantages in comparison with the prior art, amongst which, the following are pointed out:

the annoying turbulence on the inside of the spectacles is considerably reduced, the spectacles can easily be equipped for different sports disciplines simply by the fitting of different accessories, an optimal fit of the spectacles for different facial morphologies is ensured, by replacing the nose-piece with another of a different size, the spectacles can be converted for quite different uses varying from cycling to alpine and cross-country skiing; amongst other things, a different nose-piece permits different spacing of the cross-piece from the user's face to take account, for example, of the presence of the spacer, or to compensate for the pull exerted by the resilient strap, finally, the spectacles as a whole have a pleasing appearance.

What is claimed is:

1. Sports spectacles comprising a lens-carrying frame (10) with an upper cross-member (11) including two branches (11a, 11b) extending symmetrically from a central portion (12) towards respective free ends (13a, 13b), there being defined in the frame an inner side (A) facing the user in use, and an opposite, outer side (B), characterized in that both branches (11a, 11b) have, on the outer side (B), air-directing means (18) for collecting and deflecting at least part of the air-flow striking the lenses (L) and passing over the upper cross-member and for directing it along the corresponding branch (11a, 11b) towards flow-discharge means (20) disposed in a discharge position set back towards the corresponding free end (13a, 13b).

2. Spectacles according to claim 1, in which the directing means comprises, on each of the branches (11a, 11b), a surface (18) with a helical profile extending from a rim (19) for the attachment of the corresponding lens with the helix facing so as to deflect an air-flow striking the corresponding lens (L) towards the respective free end (13a, 13b).

3. Spectacles according to claim 2, in which each of the surfaces (18) with a helical profile terminates in a respective deflector (31) oriented so as to cause the air-flow to diverge away from the cross-member (11).

4. Spectacles according to claim 2, in which, starting from the central portion (12), the helical surface has a profile of increasing radius of curvature (R), the opposite rims (19) of which develop, as they extend away from the central portion (12), from an orientation almost perpendicular to the lens (L) towards an orientation almost tangential thereto.

5. Spectacles according to claim 1, in which the discharge means (20) in each discharge position comprise a through hole (30) between the outer and inner sides (B, A) of the cross-member (11).

6. Spectacles according to claims 5, in which the hole (30) is formed in the region of the deflector (31).

7. Spectacles according to claim 1, in which a respective arm (14a, 14b) is articulated to each free end (13a, 13b) of the cross-member (11), the seat for the articulation of the arm (14a, 14b) being defined in the region of the discharge means.

8. Spectacles according to claim 1, in which a spacer (50) is provided and can be fitted to the inner side (A) of the cross-member (11).

9. Spectacles according to claim 8, in which the spacer (50) can be released from the cross-member (11).

10. Spectacles according to claim 8, in which the spacer (50) is ventilated.

11. Spectacles according to claim 1 in which the spacer (50) comprises a substantially strip-like body (51) at the opposite ends of which there are two respective end elements (52) which can engage in the holes (30) in the cross-member (11) in order to restrain the spacer (50) against the cross-member.

12. Spectacles according to claim 11, in which the strip-like body (51) has a plurality of projections (54) pointing towards the inner side (A) of the cross-member (11), arranged like a comb and spaced by channels (55).

13. Spectacles according to claim 12, in which filtering means (59) are provided in at least some of the channels (55) for slowing the air-flow circulating therein.

14. Spectacles according to claim 11, in which the holes (30) constitute engagement means for respective hook-like elements (40) associated with the opposite ends of a strap (41) for holding the spectacles in the operative position.

15. Spectacles according to claim 11, in which the central portion (12) of the lens-carrying frame (10) defines a nose piece (112) which can constitute a support for the frame (10) on the user's nose, the nose-piece (112) including a pair of cheeks (115a, 115b) disposed astride a supporting region of the user's nose and means for anchoring the cheeks (115a, 115b) to the frame (10), and in which the anchoring means comprise two rod-shaped appendages (113a, 113b) which straddle the supporting region of the user's nose and each of which can be inserted in a corresponding seat (114a, 114b) formed in the respective cheek (115a, 115b) so that the cheeks are fitted at least partially on the appendages.

16. Spectacles according to claim 15, in which coupling means (116) are provided on the appendages (113a, 113b) and in the seats (114a, 114b) for restraining each cheek (115a, 115b) in its position fitted on the respective appendage.

17. Spectacles according to claim 16 in which the coupling means comprise an enlargement (116) at the free end of each appendage (113a, 113b).

18. Spectacles according to claim 15, in which the cheeks (115a, 115b) are made of resilient material.

19. Spectacles according to claim 15, in which the appendages (113a, 113b) constitute reinforcement for the nose-piece (112) for stiffening the corresponding cheeks (15a, 115b).

20. Spectacles according to claim 15, in which the appendages (113a, 113b) are formed integrally with an upper cross-member of the front frame.

21. Spectacles according to claim 15, in which the seats (114a, 114b) have an open, tubular configuration.

22. Spectacles according to claim 15, in which the cheeks (115a, 115b) are joined by a flexible bridge (118).

23. Spectacles according to claim 15, in which the cheeks (115a, 115b) are interchangeable with other cheeks of different sizes in order to adapt the spectacles to different morphological configurations of the user's face.

* * * * *